US005921778A

United States Patent [19]
Karmaker et al.

[11] Patent Number: 5,921,778
[45] Date of Patent: Jul. 13, 1999

[54] HYBRID WOVEN MATERIAL FOR REINFORCEMENT OF DENTAL RESTORATIONS

[75] Inventors: Ajit Karmaker, Wallingford; Arun Prasad, Cheshire, both of Conn.

[73] Assignee: Jeneric/Pentron Incorporated, Wallingford, Conn.

[21] Appl. No.: 09/044,440

[22] Filed: Mar. 19, 1998

[51] Int. Cl.⁶ .................................................. A61C 5/00
[52] U.S. Cl. ........................ 433/215; 433/219; 433/226; 433/224
[58] Field of Search .................................. 433/219, 224, 433/226, 222.1, 191, 220, 221, 215; 132/321

[56] References Cited

U.S. PATENT DOCUMENTS

| | | | |
|---|---|---|---|
| 4,107,845 | 8/1978 | Lee, Jr. et al. | 523/116 |
| 4,717,341 | 1/1988 | Goldberg et al. | 433/9 |
| 4,728,291 | 3/1988 | Golub | 433/215 |
| 4,770,926 | 9/1988 | Yamamura et al. | 428/224 |
| 4,799,888 | 1/1989 | Golub | 433/215 |
| 4,894,012 | 1/1990 | Goldberg et al. | 433/215 |
| 5,000,687 | 3/1991 | Yarovesky et al. | 433/180 |
| 5,074,791 | 12/1991 | Shoher et al. | 433/180 |
| 5,098,304 | 3/1992 | Scharf | 433/215 |
| 5,120,224 | 6/1992 | Golub | 433/215 |
| 5,176,951 | 1/1993 | Rudo | 428/229 |
| 5,395,683 | 3/1995 | Bledsoe et al. | 428/253 |
| 5,538,781 | 7/1996 | Rao et al. | 428/29 |
| 5,564,929 | 10/1996 | Alpert | 433/224 |

*Primary Examiner*—John J. Wilson
*Assistant Examiner*—Patrick A. Hilsmie
*Attorney, Agent, or Firm*—Cantor Colburn LLP

[57] ABSTRACT

A reinforced composite material for use in dental restorations such as dental bridges, splints, veneers, and laminate comprising a hybrid woven material formed of glass yarns and synthetic yarns. Suitable synthetic yarns comprise polyethylene, polypropylene, polyester, acrylic fibers, or a combination thereof. The hybrid woven material of the present invention does not fray upon cutting, which greatly enhances ease of preparation of the fiber-reinforced dental restorations.

39 Claims, 1 Drawing Sheet

HYBRID WOVEN MATERIAL FOR REINFORCEMENT OF DENTAL RESTORATIONS

BACKGROUND OF THE INVENTION

1. Field of the Invention

This invention relates to dental restorations and methods of manufacture thereof. In particular, this invention relates to splints, laminates, veneers, and dental bridges comprising a hybrid woven material reinforcement wherein the hybrid woven material comprises glass yarns and synthetic yarns.

2. Brief Discussion of the Prior Art

Fiber-reinforced composites have found increasing use in the field of materials for dental restorations, and are described, for example, in U.S. Pat. Nos. 4,717,341 and 4,894,012 to Goldberg et al., as well as U.S. Pat. No. 4,107,845 to Lee, Jr. et al. Fiber-reinforced composites generally comprise at least two components, a polymeric matrix and fibers embedded within the matrix. The composite materials may further comprise a filler material. Common polymeric matrices include those known for use in composite dental materials, for example polyamides, polyesters, acrylates, polyolefins, polyimides, polyacrylates, polyurethanes, vinyl esters, or epoxy-based materials. Other polymeric matrices include styrenes, styrene acrylonitriles, ABS polymers, polysulfones, polyacetals, polycarbonates, polyphenylene sulfides, and the like. The fibers used to reinforce composite material may comprise glass, carbon, or polymer fibers such as polyaramide and polyethylene, as well as other natural and synthetic fibers.

Fiber-reinforced composite materials provide several advantages, most notably increased strength and stiffness. As described in U.S. Pat. Nos. 4,717,341 and 4,894,012 to Goldberg et al., the content of which is incorporated by reference herein, such materials may be used as structural components in a variety of dental appliances, taking the form of bars, wires, beams, posts, clasps, and laminates. The fibers preferably take the form of long, continuous filaments, although the filaments may be as short as 3 to 4 millimeters. Where the composites take the form of elongated bars, the fibers are at least partially aligned and oriented along the longitudinal dimensions of the bar. However, depending on the end use of the composite material, the fibers may also be otherwise oriented, including being normal or perpendicular to that dimension. These structural components are used in traditional bridges, crowns, artificial teeth, dentures, implants, veneers as well as in connection with orthodontic retainers, space maintainers, splints, and the like.

A bridge, in particular, is a device for the restoration and replacement of one or more natural teeth, replacing at least one missing tooth and supported on either side by the remaining (abutment) teeth. A bridge generally comprises a pontic for replacement of the missing tooth, and two connectors which connect the pontic to retaining members such as crowns formed on abutment teeth adjacent the pontic. By their nature, bridges must be aesthetic, as well as strong in order to withstand forces generated by chewing and to maintain the positions of the abutting teeth. A number of bridge designs disclosed in the prior art are intended to either enhance strength or ease of preparation. For example, U.S. Pat. No. 5,074,791 discloses a bridge comprising a pre-formed pontic, which simplifies preparation. The so-called "winged bridge" disclosed in U.S. Pat. No. 5,000,687 is designed to enhance bridge strength by providing extensions ("wings") on the pontic which are adhered to the distal side of the abutment teeth. Woven fiber reinforcement for dental restorations is also disclosed in U.S. Pat. No. 4,728,291, U.S. Pat. No. 4,799,888 and U.S. Pat. No. 5,120,224, all to Golub; U.S. Pat. No. 5,098,304 to Scharf; and U.S. Pat. No. 5,176,951 to Rudo.

Other related devices that may use fiber-reinforced composites include splints, laminates, and veneers. Splints are used to provide strength and stability to loose teeth, or to temporary replacement teeth. Laminates and veneers may cover one or more teeth, and are used for aesthetic purposes. Fiber-reinforced splints, laminates, and veneers are described in the above-mentioned patents to Golub and Scharf.

While it is well known in the art to use a woven glass fabric as the fiber component of fiber-reinforced composites, a significant drawback has been the tendency of yarns of a woven and non-woven glass fabric to fray, that is to separate from the fabric when the fabric is cut. Fraying of the yarns, especially at the ends of the cut fabric, presents difficulties in the processing and use of the fabric. Glass fabric is especially prone to fraying, which severely restricts its use as a reinforcement material for dental composites. Accordingly, there remains a need for a reinforcing material comprising woven fibers that may be processed without fraying and separation of the fibers after the material has been cut.

SUMMARY OF THE INVENTION

The above-described and other problems and deficiencies of the prior art are overcome or alleviated by the hybrid woven material of the present invention, wherein the hybrid woven material comprises glass fiber yarns and synthetic fiber yarns, preferably polyethylene. Preferably, the hybrid woven material is in the form of a woven tape or braided rope, wherein the glass yarns are held in place, that is, substantially prevented from fraying upon cutting, by the interweaving or braiding of at least one synthetic yarn. The hybrid woven material of the present invention does not substantially fray upon cutting, which greatly enhances the ease of preparation of fiber-reinforced dental restorations such as bridges, splints, veneers, and the like.

BRIEF DESCRIPTION OF THE DRAWINGS

For the purpose of illustrating the invention, there are shown in the drawing forms which are presently preferred; it being understood, however, that this invention is not limited to the precise arrangements and instrumentalities shown. Referring now to the drawings wherein like elements are numbered alike in the several FIGURES:

FIGS. 4 and 5 are elevation views of maxillary anterior teeth illustrating steps in tooth replacement utilizing the hybrid tape in accordance with the present invention and illustrating another possible use wherein FIG. 4 is a lingual view and FIG. 5 is a labial view; and.

DETAILED DESCRIPTION OF THE INVENTION

The present invention is directed to a new and improved material for reinforcing dental restorations and/or splinting teeth, wherein the reinforcing material is a hybrid woven material comprising glass fiber yarns and at least one synthetic fiber yarn, preferably polyethylene. As used herein, "woven materials" is inclusive of materials which are both woven and braided, that is, materials which are in either fabric form or rope form. Further as used herein "yarns" may comprise a single fiber or multiple fibers twisted to form a unitary structure for weaving or braiding.

Figure 1:
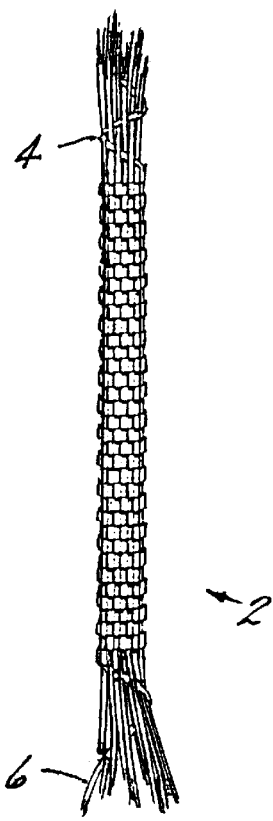
FIG. 1 is a plan view of a prior art woven tape comprising glass fibers, which has been cut, showing substantial fraying.

Use of the hybrid woven materials of the present invention prevents fraying normally associated with the cutting of a woven or braided glass material. As previously described, one drawback to the use of woven yarn materials, especially glass yarns, has been the tendency of the yarns of the material to fray substantially, that is, to separate when the material is cut. A prior art uniform mesh woven tape 2 comprising glass yarns 4 which has been cut without prior heat treatment of the fibers is shown in FIG. 1, illustrating the fraying 6 that occurs upon cutting.

Without being bound by theory, it is hypothesized that fraying is caused by the bending of the glass yarn. In a woven fabric, the yarns in the y-direction are called warp yarns, and represent the length of the fabric. The yarns in the x-direction are called fill yarns and represent the width of the fabric. The fill yarn is mechanically bent at its turning points during weaving at both edges of the fabric. The bending of the fibers is still within the elastic region of the glass, and the fibers tend to regain their original positions when the fabric is cut. When the woven glass fabric is in the cut shape of a narrow tape, the tendency for the fill yarn to separate from the fabric upon cutting is increased and consequently, the narrow tape separates at its ends.

Figure 2:
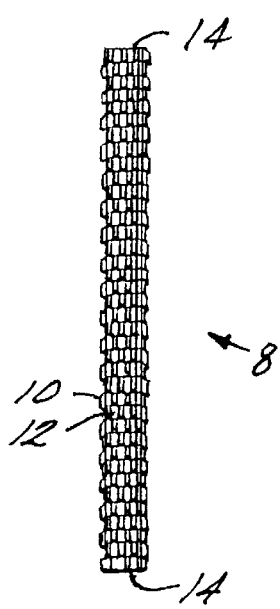
FIG. 2 is a plan view of a woven hybrid tape comprising glass and at least one synthetic yarns in accordance with the present invention after the hybrid tape has been cut.

This problem associated with the cutting of the glass fiber material is overcome or alleviated by the hybrid woven material of the present invention. FIG. 2 illustrates a uniform mesh woven tape 8 comprising glass yarns and at least one synthetic yarn. In accordance with the present invention, any fraying of the fabric upon cutting is eliminated by using synthetic yarn 10 as the fill yarn. The warp yarns 12 comprise glass yarns or a combination of both glass yarns and synthetic yarns. Where the warp yarns comprise a combination of glass and polyethylene fibers, an increase in the flexibility of the material is realized as a result of using the two fibers in combination as the warp yarns of the hybrid tape.

Figure 6:
FIG. 6 is a plan view of a braided rope having glass yarns and at least one synthetic yarn in accordance with the present invention.

FIG. 6 illustrates a rope 40 in accordance with the present invention, comprising glass yarns 42 and at least one synthetic yarn 43. While the preferred form of the hybrid woven material of the present invention is provided to the practitioner in the form of a rope or a woven tape, that is, a fabric having a length greater than its width, it is to be understood that the hybrid material may be provided to the practitioner in other forms, for example, squares of fabric, and then cut by the practitioner to the desired dimensions so long as the fabric comprises glass yarns and at least one synthetic yarn that do not fray upon cutting.

Preferably, a plurality of glass fibers are used as warp yarns in a woven hybrid tape. Suitable glasses for the practice of the present invention include those known in the art, including but not being limited to the compositions set forth in the Table below. A preferred glass formulation is known in the art as "E Glass".

| Oxide* | A-Glass | C-Glass | D-Glass | E-Glass | ECR-Glass | AR-Glass | R-Glass | S-2Glass ® |
|---|---|---|---|---|---|---|---|---|
| $SiO_2$ | 63–72 | 64–68 | 72–75 | 52–56 | 54–62 | 55–75 | 55–65 | 64–66 |
| $Al_2O_3$ | 0–6 | 3–5 | 0–1 | 12–16 | 9–15 | 0–5 | 15–30 | 24–25 |
| $B_2O_3$ | 0–6 | 4–6 | 21–24 | 5–10 | | 0–8 | | |
| CaO | 6–10 | 11–15 | 0–1 | 16–25 | 17–25 | 1–10 | 9–25 | 0–0.1 |
| MgO | 0–4 | 2–4 | | 0–5 | 0–4 | | 3–8 | 9.5–10 |
| ZnO | | | | | 2–5 | | | |
| BaO | | 0–1 | | | | | | |
| $Li_2O$ | | | | | | 0–1.5 | | |
| $Na_2O + K_2O$ | 14–16 | 7–10 | 0–4 | 0–2 | 0–2 | 11–21 | 0–1 | 0–0.2 |
| $TiO_2$ | 0–0.6 | | | 0–1.5 | 0–4 | 0–12 | | |
| $ZrO_2$ | | | | | | 1–18 | | |
| $Fe_2O_3$ | 0–0.5 | 0–0.8 | 0–0.3 | 0–0.8 | 0–0.8 | 0–5 | | 0–0.1 |
| $F_2$ | 0–0.4 | | | 0–1 | | 0–5 | 0–0.3 | |

*percent by weight

In order to enhance the bonding of the glass yarns to the polymeric composite of the dental restoration, the glass fibers or yarns may be first mechanically abraded or etched, and then treated with an organo-functional silane by means known in the art prior to being woven or braided with synthetic fibers to form the hybrid woven material. The etching of the glass fibers produces a roughened or barbed surface, which may be observed under a microscope. After the etching is completed, any suitable organo-functional silane may be utilized which is capable of enhancing the bonding between the glass fiber material and the polymeric matrix. Alternatively, the glass fibers may be silanated without etching. A number of silanizing agents are well known and examples of these include vinyltrichlorosilane, vinyltriethoxysilane, vinyl-tris(beta-methoxyethoxy)silane, gamma-methacryloxypropyltrimethoxysilane, beta-(3,4-epoxycyclohexyl)-ethyltrimethoxysilane, gamma-glycidoxypropyltrimethoxysilane, gamma-aminopropyltriethoxysilane, and N-beta-(aminoethyl)-gamma-aminopropyltrimethoxysilane.

Suitable synthetic fibers for use in the present invention include but are not limited to various polymeric materials such as polyethylene, polypropylene, polyester and acrylic fibers, or a combination thereof. When these polymeric fibers are bent, they have the characteristic of being deformed permanently and do not spring back to their original position upon cutting of the fabric. Advantageously, this characteristic of the synthetic fibers allows the hybrid material to maintain its desired shape upon cutting and thus minimize fraying.

When employed for reinforcement of a dental restoration, the hybrid woven material of the present invention is used in combination with a polymeric matrix. Polymeric matrices for use in dental restorations are known, including, but not being limited to, polyamides, acrylates, polyesters, polyolefins, polyimides, polyacrylates, polyurethanes, vinyl esters or epoxy-based materials. Other polymeric matrices include styrenes, styrene acrylonitriles, ABS polymers, polysulfones, polyacetals, polycarbonates, polyphenylene sulfides, and the like.

Preferred polymeric matrices include those based on acrylic and methacrylic monomers, for example those disclosed in U.S. Pat. No. 3,066,112, U.S. Pat. No. 3,179,623, and U.S. Pat. No. 3,194,784 to Bowen; U.S. Pat. No. 3,751,399 and U.S. Pat. No. 3,926,906 to Lee et al.; and commonly assigned U.S. Pat. No. 5,276,068 to Waknine, all of which are herein incorporated by reference in their entirety. An especially preferred methacrylate monomer is the condensation product of bisphenol A and glycidyl methacrylate, 2,2'-bis [4-(3-methacryloxy-2-hydroxy propoxy)-phenyl]-propane (hereinafter abbreviated "BIS-GMA"), the condensation product of ethoxylated bisphenol A and glycidyl methacrylate (hereinafter EBPA-DMA), and the condensation product of 2 parts hydroxymethyl-methacrylate and 1 part triethylene glycol bis (chloroformate) (hereinafter PCDMA). Polyurethane dimethacrylates (hereinafter abbreviated to PUDMA) are also commonly-used principal polymers suitable for use in the present invention.

The polymeric matrix may further comprise a co-polymerizable diluent monomer. Such monomers are generally used to adjust the viscosity of the polymerizable composition, which affects wettability of the composition. Suitable diluent monomers include, without limitation, hydroxyalkyl methacrylates, such as 2-hydroxyethylmethacrylate, 1,6-hexanedioldimethacrylate, and 2-hydroxypropylmethacrylate; glyceryl dimethacrylate; ethyleneglycolmethacrylates, including ethyleneglycolmethacrylate, diethyleneglycolmethacrylate, triethyleneglycolmethacrylate and tetraethyleneglycolmethacrylate; and diisocyanates, such as 1,6-hexamethylene diisocyanate. Triethyleneglycoldimethacrylate (TEGDMA) is particularly preferred for use in the present invention.

The polymer matrix typically includes polymerization initiators, polymerization accelerators, ultra-violet light absorbers, anti-oxidants, fluorescent whitening agents, and other additives well known in the art. The polymer matrices may be visible light curable, self-curing, dual curing, and vacuum, heat, and pressure curable compositions as well as any combination thereof. Visible light curable compositions employ light-sensitive compounds such as benzil diketones, and in particular, dl-camphoroquinone in amounts ranging from about 0.05 to 1.0 weight percent. UV absorbers are particularly desirable in the visible light curable compositions in order to avoid discoloration of the resin form any incident ultraviolet light. Suitable UV absorbers are the various benzophenones, particularly UV-9 and UV-5411 available from American Cyanamid Company, and benzotriazoles known in the art, particularly 2-(2'-hydroxy-5'-methylphenyl)-benzotriazole, sold under the trademark TINUVIN P by Ciba-Geigy Corporation, Ardsley, N.Y. in amounts ranging from about 0.05 to about 5.0 weight percent.

In the self-curing compositions, a polymerization accelerator may be included in the polymerizable monomer composition. The polymerization accelerators suitable for use include the various organic tertiary amines well known in the art, generally aromatic tertiary amines, such as dimethyl-p-toluidine, dihydroxyethyl-p-toluidine and the like, in amounts ranging from about 0.05 to about 4.0 weight percent, and generally acrylate derivatives such as dimethylaminoethyl methacrylate and particularly, diethylaminoethyl methacrylate in amounts ranging from about 0.05 to 0.5 weight percent.

The heat and pressure curable compositions, which are generally filled compositions, include, in addition to the monomeric components, a heat cure initiator such as benzoyl peroxide, 1,1'-azobis(cyclohexanecarbo-nitrile), or other free radical initiators. Particularly suitable free radical initiators are lauroyl peroxide, tributyl hydroperoxide and, more particularly benzoyl peroxide.

In addition to unfilled polymeric matrices, the polymeric matrix of the present invention can also be filled or partially filled. The filled compositions of the invention can include all of the inorganic/organic fillers currently used in dental restorative materials, the amount of such filler being determined by the specific function of the filled materials.

The filled compositions of this invention can, in general, include any suitable filler which is capable of being covalently bonded to the polymer matrix itself or to a coupling agent which is covalently bonded to both. Examples of suitable filling materials include but are not limited to, silica, silicate glass, quartz, barium silicate, strontium silicate, barium borosilicate, strontium borosilicate, borosilicate, lithium silicate, amorphous silica, ammoniated or deammoniated calcium phosphate and alumina zirconia tin oxide and titania. Particularly suitable fillers for dental filling-type materials prepared in accordance with this invention are those having a particle size ranging from about 0.1–5.0 μm with a silicate colloid of 0.001 to about 0.07 microns and prepared by a series of milling steps comprising wet milling in an aqueous medium, surface etch milling and silanizing milling in a silane solution. Some of the aforementioned inorganic filling materials are disclosed in U.S. Pat. No. 4,544,359 and U.S. Pat. No. 4,547,531, pertinent porions of which are incorporated herein by reference. The filler content in general is in the range from about 0 to 85% by weight of the total composition, depending on the use made of the polymerized composition.

One preferred polymeric matrix for use with the present invention comprises approximately 70% filler by weight, with the remaining material being BIS-GMA and TEGDMA in a ratio of about 1:1 by weight, and suitable curing agents. Another polymeric matrix usable in accordance with the present invention comprises BIS-GMA and PCDMA in a ratio of about 9:1 by weight, and suitable curing agents.

In the practice of the present invention, a polymeric matrix is applied to the restoration site prior to the application of the hybrid woven material which has been cut to the appropriate size. Preferably, the polymeric matrix is uncured and comprises initiators known in the art, for example, camphorquine. The dental restoration site may be an untreated or pretreated enamel or dentin surfaces, or an untreated or pretreated porcelain, composite, or metallic surface. The reinforcing hybrid woven material is then applied in intimate contact with the polymeric matrix. Preferably, the hybrid woven material is pre-impregnated with a polymeric matrix before application to the site of the restoration. The impregnating matrix may be uncured, partially cured, or fully cured before application. Non-impregnated hybrid woven material may also be used. Additional polymeric matrix is next applied to the dental restoration at the restoration site if required, and the restoration cured. The applied, impregnating, and additional polymeric matrices are preferably the same or compatible.

The present invention may be utilized in numerous applications in the practice of dentistry, including periodontal splinting, tooth replacement, tooth stabilization, bridge manufacture, and the like. All of these will not be described herein, as such dental operations are well known to those practicing dentistry, i.e. those of ordinary skill in the art. However, an illustration of a few of the possible uses will be illustrated in connection with the drawing figures. The operations and specific detail of the actual practice of dentistry will not be repeated as they are well known in the art.

Figure 3:
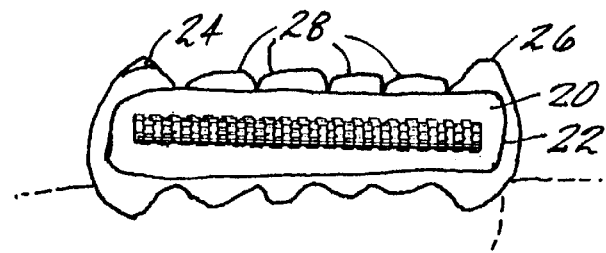
FIG. 3 is an elevation view of periodontal splinting utilizing the hybrid tape of the present invention, wherein the tape is applied to mandibular anterior teeth illustrating one use of the present invention.

Referring now to the drawings wherein like numerals indicate like elements, in FIG. 3 there is illustrated periodontal splinting of mandibular anterior teeth utilizing the hybrid tape 20 of the present invention embedded within a polymeric matrix material 22. The periodontal splinting as shown in FIG. 3 is utilized to treat mobile teeth which have lost bone support and/or which have been traumatized. As illustrated in FIG. 3, the hybrid tape 20 may be embedded in a polymeric matrix material 22 bonding together canines 24 and 26 and mandibular incisors 28.

Figure 4:
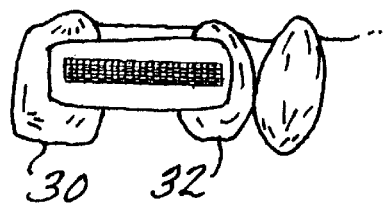
Figure 5:
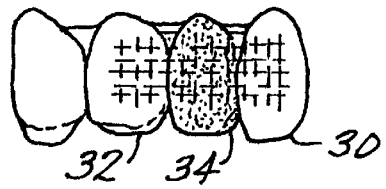

Referring now to FIGS. 4 and 5, there is shown another one of the many possible uses of the present invention in the field of dentistry in the form of an anterior tooth replacement. A polymeric matrix is applied to abutment teeth 30 and 32 which are immediately adjacent the missing tooth. The fiber-reinforced composite 31 comprising a hybrid tape embedded in a polymer matrix material is provided and applied to the restoration site on teeth 30, 32. Additional polymeric matrix may then applied to the fiber-reinforced composite. The formation of the replacement tooth 34 is now built into the mesh, polymerized and shaped into the form of a tooth, according to methods known in the art.

As shown and described above, the hybrid woven material in accordance with the present invention is more effectively processed and used in fiber-reinforced dental restorations than prior art materials. The use of the hybrid woven material alleviates the problems associated with the fraying and separation of the edges of the material when it is cut. While preferred embodiments have been shown and described, various modifications and substitutions may be made thereto without departing from the spirit and scope of the invention. Accordingly, it is to be understood that the present invention has been described by way of illustrations and not limitation.

What is claimed is:

1. A dental restoration for the restoration or stabilization of one or more teeth, comprising:
    a hybrid woven material comprising glass yarns and at least one synthetic yarn, wherein the hybrid woven material does not substantially fray upon cutting;
    a polymeric matrix material incorporated into the hybrid woven material; and
    at least one additional dental restoration component.

2. The dental restoration of claim 1, wherein:
    the at least one additional dental restoration component is selected from the group consisting of crowns, bridges, splints, laminates, and veneers.

3. The dental restoration of claim 1, wherein
    the glass yarns comprise about 52–56% $SiO_2$, 12–16% $Al_2O_3$, 5–10% $B_2O_3$, 16–25% CaO, 0–5% MgO, 0–2% $Na_2O+K_2O$, 0–1.5% $TiO_2$, 0–0.8% $Fe_2O_3$, and 0–1% fluoride.

4. The dental restoration of claim 1, wherein
    the synthetic fiber is polyethylene, polypropylene, polyester or acrylic fiber, or combinations thereof.

5. The dental restoration of claim 4, wherein
    the synthetic fiber is polyethylene fiber.

6. The dental restoration of claim 1, wherein
    the dental restoration is a splint, bridge, laminate, or veneer.

7. The dental restoration of claim 1, wherein
    the hybrid woven material comprises a fabric formed of warp yarns and at least one fill yarn, wherein
        the warp yarns comprise glass fiber or a plurality of the warp yarns comprise glass fiber and at least one warp yarn comprises synthetic fiber; and
        the at least one fill yarn consists essentially of synthetic fiber.

8. The dental restoration of claim 7, wherein
    the hybrid woven material does not substantially fray upon cutting.

9. The dental restoration of claim 7, wherein
    the glass yarns comprise about 52–56% $SiO_2$, 12–16% $Al_2O_3$, 5–10% $B_2O_3$, 16–25% CaO, 0–5% MgO, 0–2% $Na_2O+K_2O$, 0–1.5% $TiO_2$, 0–0.8% $Fe_2O_3$, and 0–1% fluoride.

10. The dental restoration of claim 7, wherein
    the synthetic fiber is polyethylene, polypropylene, polyester or acrylic fiber, or combinations thereof.

11. The dental restoration of claim 10, wherein
    the synthetic fiber is polyethylene fiber.

12. A hybrid woven material for use in dental restorations comprising:
    a plurality of yarns comprising glass fiber and at least one yarn comprising synthetic fiber, wherein the hybrid woven material does not substantially fray upon cutting.

13. The hybrid woven material of claim 12, further comprising
    a polymeric matrix material is incorporated into the hybrid woven material.

14. The hybrid woven material of claim 12, wherein
    the glass comprise about 52–56% $SiO_2$, 12–16% $Al_2O_3$, 5–10% $B_2O_3$, 16–25% CaO, 0–5% MgO, 0–2% $Na_2O+K_2O$, 0–1.5% $TiO_2$, 0–0.8% $Fe_2O_3$, and 0–1% fluoride.

15. The hybrid woven material of claim 12, wherein
    the synthetic fiber is polyethylene, polypropylene, polyester, or acrylic fiber, or a combination thereof.

16. The hybrid woven material of claim 15, wherein
    the synthetic fiber is polyethylene fiber.

17. The hybrid woven material of claim 12, wherein
    the dental restoration is a splint, bridge, laminate, or veneer.

18. The hybrid woven material of claim 12, wherein
    the hybrid woven material comprises a fabric formed of warp yarns and at least one fill yarn, wherein
        the warp yarns comprise glass fiber or a plurality of the warp yarns comprise glass fiber and at least one warp yarn comprises synthetic fiber; and
        the at least one fill yarn consists essentially of synthetic fiber.

19. The hybrid woven material of claim 18, further comprising
    a polymeric matrix material is incorporated into the hybrid woven material.

20. The hybrid woven material of claim 18, wherein
    the glass comprise about 52–56% $SiO_2$, 12–16% $Al_2O_3$, 5–10% $B_2O_3$, 16–25% CaO, 0–5% MgO, 0–2% $Na_2O+K_2O$, 0–1.5% $TiO_2$, 0–0.8% $Fe_2O_3$, and 0–1% fluoride.

21. The hybrid woven material of claim 18, wherein the synthetic fiber is polyethylene, polypropylene, polyester, or acrylic fiber, or a combination thereof.

22. The hybrid woven material of claim 21, wherein the synthetic fiber is polyethylene fiber.

23. The hybrid woven material of claim 18, wherein the dental restoration is a splint, bridge, laminate, or veneer.

24. A dental restoration for the restoration or stabilization of one or more teeth, comprising:
    a hybrid woven material comprising glass yarns and at least one polyethylene yarn; and
    a polymeric matrix material incorporated into the hybrid woven material, wherein the hybrid woven material does not substantially fray upon cutting.

25. The dental restoration of claim 24, wherein the glass yarns comprise about 52–56% $SiO_2$, 12–16% $Al_2O_3$, 5–10% $B_2O_3$, 16–25% CaO, 0–5% MgO, 0–2% $Na_2O+K_2O$, 0–1.5% $TiO_2$, 0–0.8% $Fe_2O_3$, and 0–1% fluoride.

26. The dental restoration of claim 24, wherein the glass yarns are warp yarns; and the at least one polyethylene yarn is a fill yarn.

27. The dental restoration of claim 26, wherein the hybrid woven material is in the form of a tape.

28. The dental restoration of claim 24, wherein the dental restoration is a splint, bridge, laminate, or veneer.

29. A dental restoration for the restoration or stabilization of one or more teeth, comprising:
    a hybrid woven material that does not substantially fray upon cutting, comprising a fabric formed of warp yarns and at least one fill yarn, wherein
        the warp yarns comprise glass fiber or a plurality of the warp yarns comprise glass fiber and at least one warp yarn comprises polyethylene fiber; and
        the at least one fill yarn consists essentially of polyethylene fiber; and a polymeric matrix incorporated into the hybrid woven material.

30. The dental restoration of claim 29, wherein the glass fiber is glass comprising about 52–56% $SiO_2$, 12–16% $Al_2O_3$, 5–10% $B_2O_3$, 16–25% CaO, 0–5% MgO, 0–2% $Na_2O+K_2O$, 0–1.5% $TiO_2$, 0–0.8% $Fe_2O_3$, and 0–1% fluoride.

31. The dental restoration of claim 29, wherein the fabric is in the from of a tape.

32. A method of forming a structural component for a dental restoration comprising:
    providing a hybrid woven material comprising glass yarns and at least one synthetic yarn; and
    incorporating the hybrid woven material into a polymeric matrix to form a restoration for restoring or stabilizing one or more teeth.

33. The method of claim 32, wherein the hybrid woven material does not substantially fray upon cutting.

34. The method of claim 32, wherein the glass yarns comprise about 52–56% $SiO_2$, 12–16% $Al_2O_3$, 5–10% $B_2O_3$, 16–25% CaO, 0–5% MgO, 0–2% $Na_2O+K_2O$, 0–1.5% $TiO_2$, 0–0.8% $Fe_2O_3$, and 0–1% fluoride.

35. The method of claim 32, wherein the synthetic fiber is polyethylene, polypropylene, polyester, or acrylic fiber, or a combination thereof.

36. The method of claim 32, wherein the synthetic fiber is polyethylene fiber.

37. The method of claim 32, wherein the incorporation comprises
    applying polymeric matrix to one or more teeth at a restoration site; and
    applying the hybrid woven material to the teeth over the applied polymeric matrix.

38. The method of claim 37, wherein the hybrid woven material is impregnated with polymeric matrix prior to application of the hybrid woven material to the restoration site.

39. The method of claim 38, wherein the pre-impregnated polymeric matrix is partially or fully cured after impregnation of the hybrid woven material but before application to the site of restoration.

* * * * *